US006485915B1

(12) United States Patent
Keller et al.

(10) Patent No.: US 6,485,915 B1
(45) Date of Patent: Nov. 26, 2002

(54) ANALYTICAL ELEMENT FOR SPECIES-SPECIFIC DETECTION OF NUCLEIC ACIDS

(75) Inventors: Volker Keller, Bergisch Gladbach; Andreas Rauscher, Ludwigshafen; Joachim Steinbiss, Lorsch; Reiner Schlipfenbacher, Bad Durkheim; Jurgen Klepp, Karlsruhe, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/716,013

(22) Filed: Nov. 17, 2000

(30) Foreign Application Priority Data

Nov. 25, 1999 (DE) .......................... 199 56 820

(51) Int. Cl.$^7$ ............................ C12Q 1/68; C12M 1/34; B01L 11/00; G01N 33/00
(52) U.S. Cl. .................. 435/6; 435/287.7; 436/94; 422/56; 422/61; 422/68.1; 422/101
(58) Field of Search .................. 435/6, 810, 287.7; 436/94; 422/56, 61, 68.1, 101

(56) References Cited

U.S. PATENT DOCUMENTS

| | | | | |
|---|---|---|---|---|
| 4,652,517 A | * | 3/1987 | Scholl et al. ................. | 435/5 |
| 4,740,468 A | * | 4/1988 | Weng et al. .................. | 435/7 |
| 4,960,691 A | * | 10/1990 | Gordon et al. ................ | 435/6 |
| 5,310,650 A | * | 5/1994 | McMahon et al. ............. | 435/6 |
| 5,527,673 A | * | 6/1996 | Reinhartz et al. ............. | 435/6 |
| 6,037,127 A | * | 3/2000 | Ebersole et al. .............. | 435/6 |

FOREIGN PATENT DOCUMENTS

| | | | | |
|---|---|---|---|---|
| EP | 0926498 A1 | 6/1999 | ........ | G01N/33/558 |
| WO | WO87/06621 | 11/1987 | ............ | C12Q/1/68 |

OTHER PUBLICATIONS

Cynthia Jou, et al., "Deletion Detection In The Dystrophin Gene By Multiplex Gap Ligase Chain Reaction And Immunochromatographic Strip Technology" Human Mutation 5:86–93 (1995).
Jeffrey Van Ness, et al., "The Use Of Oligodeoxynucleotide Probes In Chaotrope–Based Hydridization Solutions" Nucleic Acids Research, vol. 19 5143–5151.
Avraham Reinhartz, et al., A Novel Rapid Hybridization Technique: Paper Chromatography Hybridization Assay (PACHA) Gene, 136 (1993) 221–226 1993 Elsevier Science Publishers B.V.
Geoffrey S. Rule, et al., "Rapid Method For Visual Identification Of Specific DNA Sequences Based On DNA–tagged Liposomes" Clinical Chemistry 42.8, 1206–1209 (1996).
James Thompson, et al., "Molecular Hybridization With RNA Probes In Concentrated Solutions Of Guanidine Thiocyanate" Analytical Biochemistry 163, 281–291 (1987).

* cited by examiner

Primary Examiner—Kenneth R. Horlick
(74) Attorney, Agent, or Firm—Brent A. Harris; Jill L. Woodburn

(57) ABSTRACT

The present invention concerns a method for the detection of nucleic acids on an analytical element which contains a sample application zone and a detection zone, the analytical element enabling liquid transport from the sample application zone to the detection zone, wherein a sample is applied to the sample application zone of the analytical element and the nucleic acids contained in the sample are denatured and can be detected qualitatively in the detection zone by hybridization with a detection probe and also quantitatively, preferably by means of marker groups. In addition new analytical elements and reagent kits for the detection of nucleic acids are provided.

46 Claims, 3 Drawing Sheets

SEQUENCE LISTING

```
<160> NUMBER OF SEQ ID NOS: 3

<210> SEQ ID NO 1
<211> LENGTH: 21
<212> TYPE: DNA
<213> ORGANISM: Chlamydia trachomatis plasmid pCTT1
<220> FEATURE:
<222> LOCATION: 354-374
```

```
<400> SEQUENCE: 1 gtc tct cat cga gac aaa gtg                                                    21

<210> SEQ ID NO 2
<211> LENGTH: 25
<212> TYPE: DNA
<213> ORGANISM: Chlamydia trachomatis plasmid pCTT1
<220> FEATURE:
<222> LOCATION: 195-219

<400> SEQUENCE: 2
gggattcctg taacaacaag tcagg                                                    25

<210> SEQ ID NO 3
<211> LENGTH: 26
<212> TYPE: DNA
<213> ORGANISM: Chlamydia trachomatis plasmid pCTT1
<220> FEATURE:
<222> LOCATION: 401-376

<400> SEQUENCE: 3
cctcttcccc agaacaataa gaacac                                                   26
```

ANALYTICAL ELEMENT FOR SPECIES-SPECIFIC DETECTION OF NUCLEIC ACIDS

CROSS-REFERENCE TO RELATED APPLICATION

This application claims priority under 35 U.S.C. §119 of German Application Ser. No. 199 56 820.0 filed Nov. 25, 1999.

BACKGROUND AND SUMMARY OF THE INVENTION

The present invention concerns a method for the detection of nucleic acids on an analytical element which contains a sample application zone and a detection zone, the analytical element enabling liquid transport from the sample application zone to the detection zone, wherein a sample is applied to the sample application zone of the analytical element and the nucleic acids contained in the sample can be detected qualitatively in the detection zone by hybridization with a detection probe and also quantitatively, preferably by means of marker groups. In addition new analytical elements and reagent kits for the detection of nucleic acids are provided.

Nucleic acids such as amplification products from a PCR are currently detected for diagnostic applications by specific hybridization of the nucleic acid to be detected with a detection probe which is usually an oligonucleotide and a non-radioactive detection reaction using marker groups that can be present in the nucleic acids to be detected or/and in the detection probe. A variety of different methods can be used for this detection reaction. Thus the nucleic acids to be detected can be directly hybridized with a detection probe immobilized on a solid phase such as a microtitre plate (Amplicor Detection Kit, Roche Diagnostics, EP-A-0 420 260). Furthermore the nucleic acid to be detected can be pre-hybridized with a labelled detection probe and the complex that is formed in this process can be captured on a solid phase such as a microtitre plate (PCR-Detection Kit, Roche Diagnostics).

The use of test strips in diagnostic procedures has been known for a long period. Thus the detection of analytes using test strips is described in EP-B-0 186 799, EP-B-0 262 328 and EP-A-0 926 498 which primarily concern immunological test formats.

Jou et al. (Human Mutation 5 (1995), 86–93) describe a method for the detection of nucleic acids on chromatographic test strips in which hapten groups are introduced into the nucleic acid to be detected to enable an immunological immobilization of the nucleic acids to be detected on test strips by means of anti-hapten antibodies. Capture of nucleic acids to be detected by specific hybridization to immobilized detection probes on test strips is described for example in U.S. Pat. No. 5,310,650, EP-B-0 612 354 and Reinhartz et al. (Gene 13.6 (1993), 221–226) and Rule et al. (Clin. Chem. 42 (1996), 1206–1209).

However, the above-mentioned methods in which the detection of nucleic acids on test strips is described have a number of disadvantages. Thus the sensitivity decreases when the nucleic acid is immobilized by means of sandwich complexes. Increasing sensitivity for example by increasing the test volume is limited by the restricted incorporation of marker groups into the nucleic acids to be detected.

However, it is not possible to directly detect nucleic acids using the said methods. The complex between target nucleic acid and hybridization probe is firstly formed in a preliminary step. For this purpose the target nucleic acid is denatured (by heat treatment or by adding an alkaline solution), neutralized if necessary, the probe is added and hybridization conditions are set up. The actual detection on the test carrier can only occur after this preprocessing. Since this pre-processing involves the dosed addition of reagents and the use of apparatus e.g. heating devices, it is not possible to utilize the essential advantages of test strip-based methods such as low requirement for apparatus, simple handling, few operating steps and the ability to carry out the method by untrained persons. Furthermore these additional steps result in a risk of contamination which, in the case of detecting amplified nucleic acids, can lead to false-positive results.

Also in the case of methods which allow a direct hybridization of the nucleic acid to be detected to a hybridization probe on the analytical element, no sensitive test procedures are known in the prior art which do not require pre-processing of the nucleic acid to be detected so that in these procedures the nucleic acid cannot be detected directly or not be detected directly after an amplification process. In these procedures the target nucleic acid, which is usually present in a double-stranded form, is converted into a single-stranded conformation for the hybridization. Several methods have been described for this. Thus according to the well-known hybridization methods the nucleic acid is completely denatured, for example by heat treatment or by adding alkaline reagents, before it is applied to the analytical element. Enzymatic methods are also known which enable a specific digestion of one strand of the target nucleic acid.(Rule et al. Clinical Chemistry 42, page 1206–1209 (1996)).

Pre-processing can only be omitted when the target nucleic acids are already completely present as single strands. However, this usually already leads to difficulties when detecting ribosomal target nucleic acids because large regions of the native secondary structure of these single-stranded nucleic acids are in a double-stranded form (for example RRNA). A theoretical alternative would be amplification methods which allow a specific synthesis of only one nucleic acid strand. An example of this is asymmetric PCR. However, this method is considerably less efficient than conventional PCR methods due to the linear amplification, the sensitivity is severely limited and inadequate for the detection of analytes that are only present at a low concentration. Thus methods known in the prior art which allow a direct hybridization of the nucleic acid to be detected on the analytical element also have the same disadvantages that are found with the indirect detection methods.

A major advantage of the invention is that the previously described preprocessing of the nucleic acid to be detected can be omitted and that the nucleic acids can be applied directly to an analytical element or after an amplification process. The reagents on the analytical element that are preferably impregnated enable a complete or partial denaturation of the target nucleic acid on the analytical element which also enables hybridization of nucleic acids that are applied in a double-stranded conformation. The invention offers several possibilities for this. Thus denaturing reagents can be placed beforehand on the test carrier at a suitable concentration and preferably in a dry form in order to completely denature the nucleic acids. The target nucleic acid can be applied to the analytical element in a liquid form, for example contained in the PCR reaction solution.

After the reagents have been dissolved, the target nucleic acid is completely denatured. Since hybridization to the probe oligonucleotide cannot take place under these conditions, the chemical medium must be changed appropriately while the analyte is transported, preferably chromatographically, through the test carrier. This can on the one hand be achieved by suitable chromatography buffers or by reagents that have been placed downstream. Denaturation by means of a base and in particular NAOH and neutralization by means of an acid is preferred for this. Alternatively the chemical medium can be adjusted such that the double-stranded conformation of the target nucleic acid is destabilized (partially denatured) and hybridization to the probe oligonucleotide is enabled or facilitated. A change of the chemical medium during chromatography is unnecessary in this method variant. Preferred reagents for this embodiment are chaotropic salts and particularly preferably guanidinium thiocyanate (GuSCN).

In order to detect the target nucleic acids hybridized to the probe oligonucleotide, it is additionally necessary to label the complex. The marker groups can be incorporated into the amplified target nucleic acid by means of enzymatic incorporation during an optional amplification process that is carried out beforehand or be bound to the target nucleic acid by hybridizing an additional appropriately labelled probe oligonucleotide.

It was surprisingly found that when the method described above is used, target nucleic acids which are applied to the analytical element in a double-stranded form hybridize very effectively to the probe oligonucleotide despite the very short time that is available during chromatographic transport of the target nucleic acid over the analytical element and can be detected with high sensitivity.

DETAILED DESCRIPTION OF THE INVENTION

Figure 1:
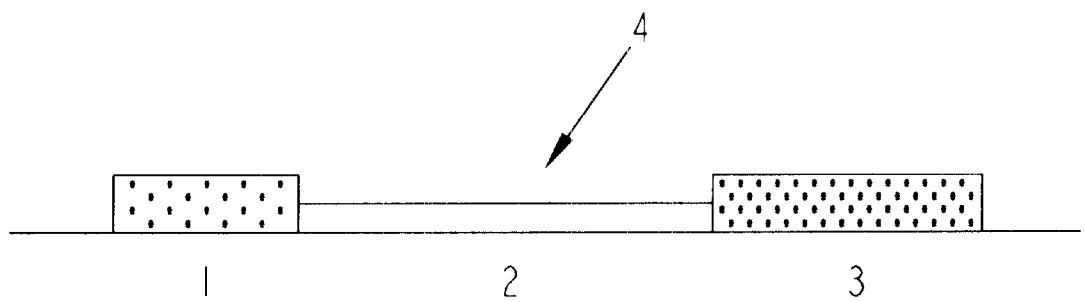
FIG. 1 is a schematic view of a test strip according to the invention.

Hence a subject matter of the invention is a method for the detection of nucleic acids on an analytical element which contains a sample application zone and a detection zone, the analytical element enabling liquid transport from the sample application zone to the detection zone, comprising the steps:

applying a sample containing the nucleic acids to be detected to the sample application zone, detecting the nucleic acid in the detection zone by hybridization with a detection probe, characterized in that the nucleic acids to be detected are denatured on the analytical element.

"Denaturation" as used herein is not only understood as a complete denaturation in the classical sense but it is also intended to include a partial denaturation in the process of which a nucleic acid double strand is destabilized to a sufficient extent to enable hybridization with a probe. Hence it is not necessary to completely dissociate the double strand although of course such an embodiment is also encompassed by the invention.

According to the invention the nucleic acids to be detected are denatured on the analytical element i.e. the nucleic acids are applied to the analytical element in a non-denatured, preferably double-stranded form and do not come into contact with the denaturing reagent until after they have been applied to the analytical element. The denaturing reagent can contain a base or/and a chaotropic substance in a quantity that is adequate to denature nucleic acids present in the sample. Preferred examples of bases are alkali hydroxides, in particular NAOH. Preferred examples of chaotropic substances are iodides, acetates, perchlorates, thiocyanates, trifluoroacetates, trichloroacetates or/and guanidinium compounds. Guanidinium thiocyanate is particularly preferred. The use of chaotropic substances on the one hand destabilizes double strands and accelerates the hybridization between the nucleic acids to be detected and detection probe. A further important function is that they lower the specific melting point of the nucleic acid which allows a specific hybridization at room temperature.

This effect of chaotropic substances is already known for hybridizations in solutions (WO-A-87 06621, Thompson and Gillespie, Anal. Biochem. 163 (1987), 281–291; Van Ness and Chen, Nucleic Acid Res. 19 (1991), 5143–5151), but is utilized for the first time in the scope of the present invention for the detection of nucleic acids by hybridization on analytical elements. An application of this technique to an analytical element would not have been obvious to a person skilled in the art because the prior art recommends hybridization times of the order of magnitude of about one hour. However, with the analytical elements according to the invention, the examination from sample application to detection is already completed after less than 10 minutes. Hybridization with the detection probe already occurs during chromatographic transport of the sample to the detection zone such that the probe and sample are only in contact for a few seconds and in any case for less than 1 min.

An essential feature of the analytical element according to the invention is that liquid can move within the analytical element from the sample application zone towards the detection zone. Such a flow of liquid can for example be achieved by gravitational force in a suitably constructed hollow body. Devices which enable liquid transport by centrifugal force as a type of gravitational force are known for example from EP-B-0 052 769. However, analytical elements according to the invention preferably contain absorbent materials which are capable of moving liquid by capillary force. The materials of the individual zones of the analytical element according to the invention can in this case be the same or different. It will frequently be the case that different zones are composed of different materials in order to function optimally.

Possible absorbent, capillary-active materials are basically all those that can be used for liquid uptake in so-called "dry tests" as described for example in U.S. Pat. Nos. 4,861,711, 5,591,645 or EP-A-0 291 194. Porous materials such as membranes e.g. nitrocellulose membranes have proven to be advantageous for this. It is, however, also possible to use fibrous absorbent matrix materials such as fleeces, fabrics or knitted fabrics. Fleeces are particularly preferred. Fibrous matrix materials can contain glass, cellulose, cellulose derivatives, polyester, polyamide and also viscose, cell wool or/and polyvinyl alcohol. Fleeces made of fibres based on cellulose, polymer fibres based on polyester and/or polyamide and an organic binding agent which has OH and/or ester groups as known from EP-B-0 326 135 can for example be used in the invention. Fleece materials containing meltable copolyester fibres, cellulose fibres or cellulose derivative fibres as described in the European Patent Application 0 571 941 can also be used in the analytical element according to the invention. Papers such as teabag paper can also be readily used.

In order to improve the handling of the analytical element according to the invention the absorbent capillary-active material or the various absorbent capillary-active materials can be arranged on a stiff support material which in turn is impermeable to liquid but does not adversely influence the liquid flow in the matrix material and behaves inertly with respect to the reactions that occur in the analytical element. Polyester foil on which the matrix material enabling liquid transport is attached can for example be a preferred support material.

The individual zones in the analytical element according to the invention can be arranged above one another, next to one another or partly above one another and partly next to one another on the support material. An analytical element according to the invention is particularly preferred in which the sample application zone and detection zone are located next to one another on the support material. In this context next to one another means that these zones are in direct contact with one another or arranged essentially in one plane separated by other zones.

The sample application zone is the region of the analytical element according to the invention on which the sample is applied. The detection zone is the region of the analytical element according to the invention in which it is determined whether the analyte to be examined or the substance derived from or representing the analyte was present in the sample that was applied to the analytical element. This determination can be qualitative, semi-quantitative or quantitative. In this connection semi-quantitative means that a specific concentration value is not determined for the analyte or the substance derived from or representing the analyte but rather a concentration range in which the analyte concentration islocated.

In a first embodiment of the invention the analytical element is impregnated with denaturing reagent before applying the sample. The denaturing reagent can be present on the analytical element and preferably on its sample application zone in a liquid or dry form. The denaturing reagent is preferably present in a dry form. In a further embodiment the analytical element is not impregnated with the denaturing reagent until after the sample is applied. Contact of the nucleic acids present in the sample to be detected with the denaturing reagent results in a denaturation of nucleic acid double strands which enables hybridization of the resulting nucleic acid single strands with the detection probe. If the denaturing reagent contains a base, it may be expedient for the analytical element to contain a neutralizing reagent, preferably in a dry form, between the sample application zone and detection zone e.g. a salt which reacts acidically on contact with liquids such as a hydrogen phosphate or a hydrogen sulphate.

The detection probe used to bind nucleic acids to be detected that are present in the sample is preferably an oligonucleotide Which contains a sequence that is sufficiently complementary to the nucleic acids to be detected to enable hybridization under the test conditions. The detection probe is preferably an oligodeoxyribonucleotide, but it is also possible to us, nucleic acid analogues containing modified nucleotide building blocks or peptidic nucleic acids as detection probes. The detection probe is preferably present in the detection zone in an immobilized form i.e. it is essentially not eluted from the detection zone under the test conditions. Immobilization can be achieved by applying the detection probe and subsequently fixing it by means of suitable methods e.g. temperature elevation, irradiation etc. Alternatively the probe can also be immobilized in the detection zone by means of high-affinity interactions e.g. biatin/streptavidin or avidin or hapten/anti-hapten antibody, sugar/lectin. Preparation of suitably modified, e.g. biotinylated detection probes, is familiar to a person skilled in the art and does not need to be elucidated in detail here. Alternatively hybridization between the nucleic acids to be detected and the detection probe can also occur upstream of the detection zone and the hybridization complex can be immobilized selectively in the detection zone during its transport through the analytical element e.g. by means of high-affinity interactions as described before.

The nucleic acids are preferably detected by means of marker groups whereby basically all marker groups known from the prior art are suitable. Visually detectable marker groups are preferred such as enzyme labels, but in particular particulate labels such as gold or latex particles. In this case the label can be located directly on the nucleic acids to be detected (direct label) but they can also be bound indirectly to the nucleic acids e.g. by means of high-affinity interactions as described above, for example via hapten/anti-hapten antibody (indirect label). The binding of indirect marker groups to the nucleic acids to be detected can occur during hybridization or not until after a wash step.

The present invention provides a simple method for the detection of nucleic acids on test strips. The nucleic acids to be detected are preferably amplification products e.g. amplification products that have been produced by a PCR. In this case the amplification products can be applied to the test strip directly using the buffer solution in which the amplification reaction has been carried out as a chromatographic solvent.

A further subject matter of the invention is an analytical element for the detection of nucleic acids which contains a sample application zone and a detection zone, the analytical element enabling liquid transport from the sample application zone to the detection zone which is impregnated with a denaturing reagent for nucleic acids and the denaturing reagent is preferably present in a dry form. The analytical element can contain an absorbent material which enables chromatographic transport and is preferably constructed as a test strip. A detection probe that is complementary to the nucleic acids to be detected is preferably present in an immobilized form in the detection zone of the analytical element.

Finally the invention concerns a kit for the detection of nucleic acids comprising an analytical element according to the invention and additional reagents required to detect nucleic acids e.g. reagents, buffers etc.

The method, analytical elements and reagent kits provided by the present invention are particularly suitable for the detection of nucleic acid amplification products e.g. for detecting the presence or amount of selected organisms or parts of organisms e.g. cells in a sample. For this purpose it is for example possible to carry out a genus-specific and species-specific detection of nucleic acids in a sample e.g. by amplification of ribosomal RNA or a DNA sequence coding therefor from organisms or cells occurring in a sample. The method can be used to detect microorganisms e.g. pathogenic microorganisms or viruses in clinical samples, foods, water samples etc. Furthermore the method can also be used for forensic analysis to detect specific individuals. The detection of nucleic acids derived from Chlamydia trachomatis by means of the method according to the invention is shown in the following examples.

Figure legends:

FIG. 1 shows the schematic structure of a test strip according to the invention containing a sample application zone (1) which is designed as an absorbent fleece, a liquid transport zone (2) containing a detection zone (4) that is located therein and an absorbent zone (3) which is also designed as an absorbent fleece.

Figure 2A:
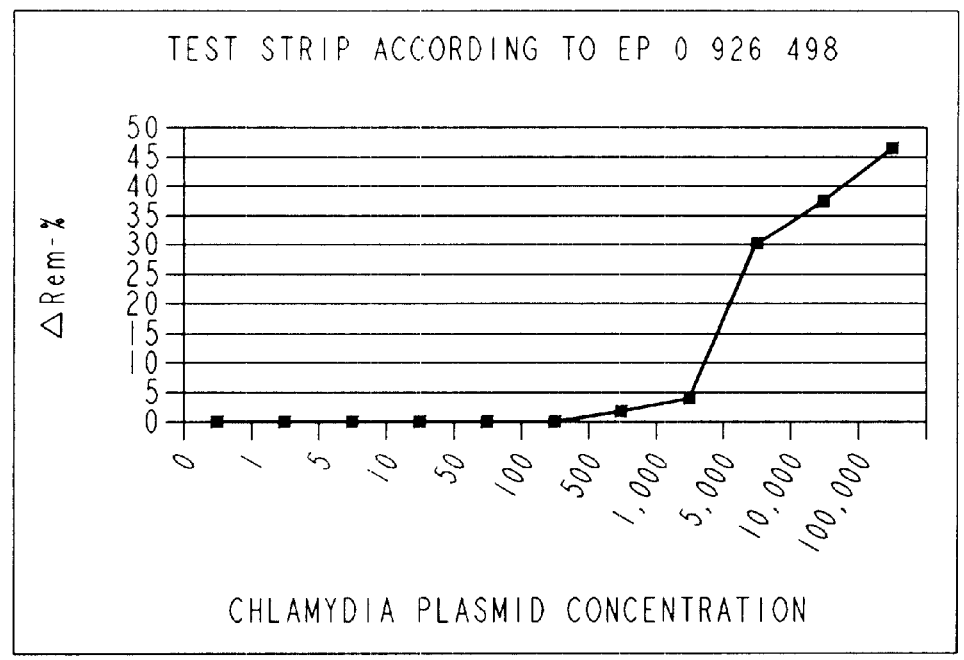
FIG. 2a is a graph showing the sensitivity of the method described in the prior art.
Figure 2B:
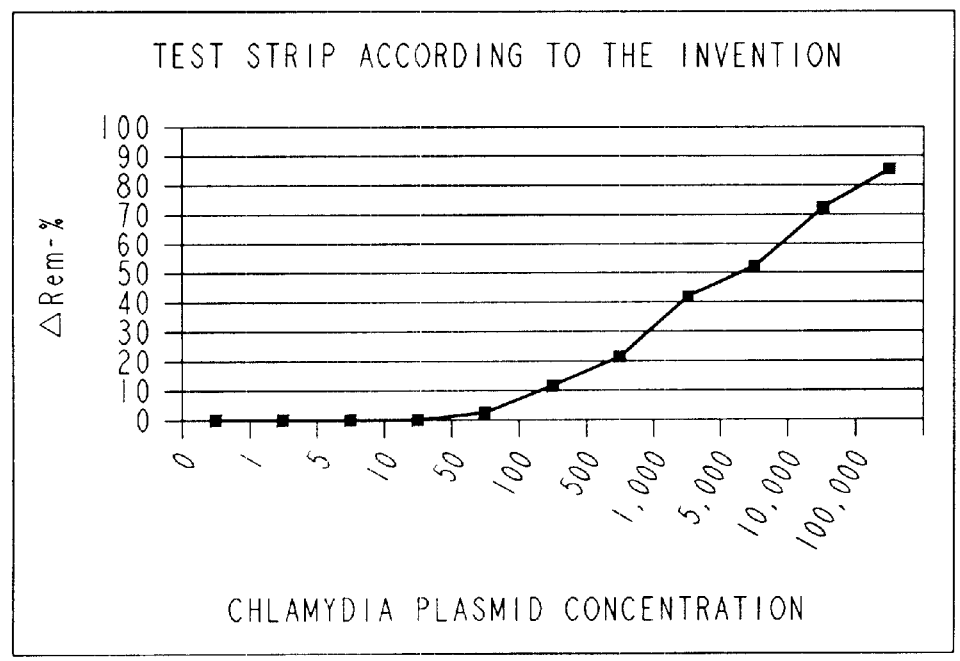
FIG. 2b is a graph showing the sensitivity of the method according to the invention.

FIGS. 2A and 2B show a comparison between the sensitivity of the method according to the invention (2B) and the method (2A) described in EP-A-0 926 498.

Figure 3:
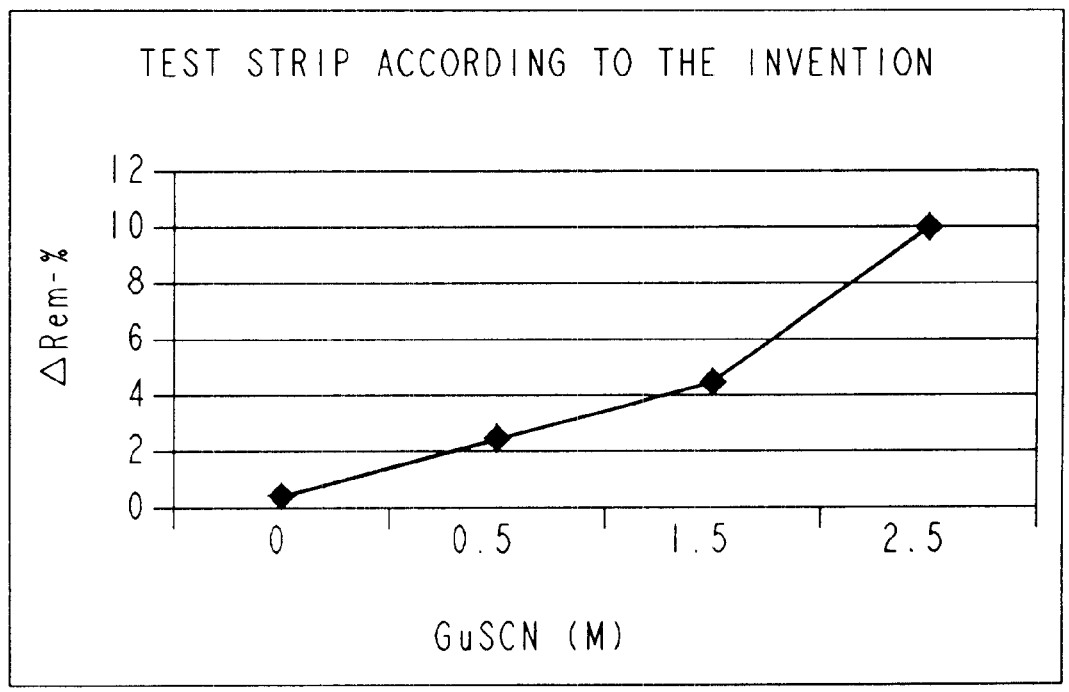
FIG. 3 is a graph showing the relationship between the sensitivity of an analytical element and guanidinium thiocyanate concentration.

FIG. 3 shows the relationship between the sensitivity of an analytical element and the guanidinium thiocyanate (GUSCN) concentration.

EXAMPLE 1

Conception

1. Preparation of the Analytical Element

The absorbent fleece (1) of the analytical element shown in FIG. 1 was impregnated with impregnation buffer (10 mM $KPO_4$ pH 7.5, 100 mM NaCl, 2 or 2.5 M guanidinium thiocyanate (CUSCN), 0.5% Triton-X100, 25 mM NAOH, 2% RPLA type 4 (Roche Diagnostics, cat. No. 1726544-106) and 3 mg/ml herring sperm DNA). For this purpose the absorbent fleece was completely wetted with impregnation buffer in a petri dish and dried for 3 h at 45° C. under circulating air.

A 15 mm nitrocellulose membrane was used as the liquid transport zone (2). The detection zone (4) was prepared by applying detection oligonucleotide probes (40 pmol per test strip) to the membrane. For this a solution of the oligonucleotides (200 µM) was applied in the form of a detection line using an automatic dispenser (Hamilton Microlab N) and the oligonucleotides were immobilized on the membrane for 30 min at 80° C. Alternatively biotin-labelled oligonucleotides were applied to a detection zone (4) that was precoated with polystreptavidin. For this an oligonucleotide solution (8 pmol/test strip) was applied to the nitrocellulose membrane and chromatographed over the detection zone precoated with polystreptavidin using 10 µl standard chromatography buffer.

An oligonucleotide with SEQ ID NO. 1, that being 5'-GTC TCT CAT CGA GAC AAA GTG-3' from the *Chlamydia trachomatis* plasmid PCTT1 (*C. trachomatis* bases 1–7496} corresponding to position 354–374 of PCTT1 was used as the detectionprobe (Sriprakash and Macavoy, Plasmid 18 (1987), 205–214).

2. PCR Protocol

The oligonucleotides SEQ ID NO. 2, that being CP24 5'-GGGATTCCTGTAACAACAAGTCAGG-3' (position 195–219 of PCTT1) and -SEQ ID NO. 3, that being-CP27:5'-CCTCTTCCCCAGAACAATAAGAACAC-3' (position 401–376 of PCTT1) were used as primers for the amplification optionally in a 5'-biotinylated or 5'-digoxigenylated form.

The reaction volume was 100 µl (4 mM $MgCl_2$, 0.1 mM DNTP each time, 300 nM primer CP24 and CP27 each, 2.5 U Taq polymerase, 2 U UNG (uracil DNA glycosylase) and template in PCR buffer (Roche Diagnostics catalogue No. 1600753).

The reaction sequence was as follows:

10 min at 37° C., 5 min at 95° C., 1 min at 60° C.

34 cycles of 30 s at 95° C. and 60 s at 60° C.

10 min at 72° C.

keep at 50° C.

The PCR reaction was carried out with various amounts of template (0 to 100 000 plasmid copies per mixture).

3. Detection

50 µl amplificate (example 2) was appolied to the absorbent fleece of the test strip and chromatographed for 4 min. Subsequently 30 µl standard chromatography buffer (0.15 M NaCl, 9.6 mM $KH_2PO_4$, 40.5 mM $K_2HPO_4$, 0.25% Tween 20, 2% RPLA type 4, 0.09% sodium azide) was applied and chromatographed for 4 min. Afterwards 20 µl anti-digoxigenin antibody gold conjugate solution (2.1 pmol) was applied and chromatographed for 4 min. Then 50 µl standard chromatography buffer was applied twice and chromatographed for 4 min.

The results of this experiment are shown in FIGS. 2A and 2B. FIG. 2A shows the result using a test strip according to EP-A-0 926 489 in which the nucleic acid is detected by immunological methods using a sandwich format. FIG. 2B shows the result of a detection method according to the invention using a test strip according to example 1. Whereas a lower sensitivity (detection only of 1000 copies or more of plasmid per mixture) was found with the test strip according to FIG. 2A, a detection of a considerably lower plasmid copy number (50) was already possible with the method according to the invention. In general, the detection signal is found to be positive if ΔRem-% is equal to or grater than 3. In addition to the higher sensitivity, the method according to the invention also has a much larger dynamic range i.e. a significant change of signal over a larger concentration range of the nucleic acid to be detected.

EXAMPLE 2

Analytical elements according to FIG. 1 were prepared according to example 1.1 with the exception that the impregnation buffer of the absorbent fleece contained no NaOH. Guanidinium concentrations of 0.5 M, 1.5 M and 2.5 M (near to the saturation limit) were tested.

50 µl PCR amplificate (100 plasmids per mixture) were applied to each of the analytical elements which were prepared according to example 1.2. Detection was carried out according to example 1.3.

The results are shown in FIG. 3. It can be seen that the addition of guanidinium thiocyanate significantly improves the detection sensitivity.

What is claimed is:

1. A method for the detection of nucleic acids comprising the steps of:
    providing an analytical element containing a sample application zone and a detection zone, the analytical element enabling liquid transport from the sample application zone to the detection zone,
    applying a sample containing the nucleic acids to be detected to the sample application zone,
    denaturing the nucleic acids to be detected on the analytical element, and
    detecting the nucleic acids in the detection zone by hybridization with a detection probe.

2. Method as claimed in claim 1, wherein the analytical element contains an absorbent material which enables a chromatographic transport.

3. Method as claimed in claim 1, wherein the analytical element contains a neutralizing reagent between the sample application zone and the detection zone.

4. Method as claimed in claim 1, wherein the nucleic acids to be detected are amplification products.

5. Method as claimed in claim 1, wherein the detection probe is present in an immobilized form in the detection zone.

6. Method as claimed in claim 1, wherein the denaturing step includes contacting the nucleic acids with a denaturing reagent containing a base.

7. Method as claimed in claim 6, wherein the base is selected from the group consisting of alkali hydroxides.

8. Method as claimed in claim 7, wherein the base is sodium hydroxide.

9. Method as claimed in claim 1, wherein the denaturing step includes contacting the nucleic acids with a denaturing reagent containing a base and a chaotropic substance.

10. Method as claimed in claim 9, wherein the chaotropic substance is selected from the group consisting of iodides, acetates, perchlorates, thiocyanates, trifluoroacetaes, trichloracetates, and guanidinium compounds.

11. Method as claimed in claim 1, wherein the denaturing step includes contacting the nucleic acids with a denaturing reagent containing a chaotropic substance.

12. Method as claimed in claim 11, wherein the chaotropic substance is guanidinium thiocyanate.

13. Method as claimed in claim 11, wherein the chaotropic substance is selected from the group consisting of iodides, acetates, perchlorates, thiocyanates, trifluoroacetaes, trichloracetates, and guanidinium compounds.

14. Method as claimed in claim 1, further comprising the step of impregnating the analytical element with the denaturing reagent before applying the sample.

15. Method as claimed in claim 14, wherein the denaturing reagent is present in a dry form on the analytical element.

16. Method as claimed in claim 1, further comprising the step of impregnating the sample application zone with the denaturing reagent before applying the sample.

17. Method as claimed in claim 1, further comprising the step of impregnating the analytical element with the denaturing reagent after applying the sample.

18. Method as claimed in claim 1, wherein the detecting step includes detecting the nucleic acids with marker groups.

19. Method as claimed in claim 18, wherein the detecting step includes detecting the nucleic acids with indirect marker groups.

20. An analytical element for the detection of nucleic acids comprising:
    a sample application zone,
    a detection zone, and
    a denaturing reagent for nucleic acids impregnated in the element, wherein the analytical element is formed to enable liquid transport from the sample application zone to the detection zone.

21. Analytical element as claimed in claim 20, wherein the denaturing reagent is present in a dry form.

22. Analytical element as claimed in claim 20, further comprising an absorbent material in the element that enables a chromatographic transport of liquid from the sample application zone.

23. Analytical element as claimed in claim 20, wherein the analytical element designed as a test strip.

24. Analytical element as claimed in claim 20, wherein the detection zone contains a detection probe in an immobilized form that is complementary to the nucleic acids to be detected.

25. Analytical element as claimed in claim 20, wherein the denaturing reagent contains a base.

26. Analytical element as claimed in claim 25, wherein the base is selected from the group consisting of alkali hydroxides.

27. Analytical element as claimed in claim 20, wherein the denaturing reagent contains a base and a chaotropic substance.

28. Analytical element as claimed in claim 27, wherein the chaotropic substance is selected from the group consisting of iodides, acetates, perchlorates, thiocyanates, trifluoracetates, trichloracetates, and guanidinium compounds.

29. Analytical element as claimed in claim 20, wherein the denaturing reagent contains a chaotrople substance.

30. Analytical element as claimed in claim 29, wherein the chaotropic substance is selected from the group consisting of iodides, acetates, perchlorates, thiocyanates, trifluoracetates, trichloracetates, and guanidinium compounds.

31. Analytical element as claimed in claim 20, wherein denaturing reagent is impregnated in the sample application zone.

32. Analytical element as claimed in claim 20, further comprising a neutralizing reagent between the sample application zone and the detection zone.

33. Analytical element as claimed in claim 20, further comprising a detection probe present in an immobilized forming in the detection zone.

34. A kit for the detection of nucleic acids comprising:

an analytical element including a sample application zone, a detection zone, and a denaturing reagent for nucleic acids impregnated in the element, wherein the analytical element is formed to enable liquid transport from the sample application zone to the detection zone, and additional reagents required to detect nucleic acids.

35. Method for detecting nucleic acid amplification products, comprising contacting a sample to be tested with the denaturing reagent from the kit of claim 34 to denature the nucleic acids to be detected, and detecting the nucleic acids by hybridization with a detection probe.

36. Method for detecting the presence of selected organisms or parts of organisms in a sample, comprising contacting a sample to be tested with the denaturing reagent from the kit of claim 34 to denature the selected organisms to be detected, and detecting the presence of the selected organisms by hybridization with a detection probe.

37. Method for detecting the amount of selected organisms or parts of organisms in a sample, comprising contacting a sample to be tested with the denaturing reagent from the kit of claim 34 to denature the selected organisms to be detected, and detecting the amount of selected organisms by hybridization with a detection probe.

38. An analytical element for the detection of nucleic acids comprising:

a sample application zone, a detection zone, a liquid transport zone formed to transport liquid from the sample application zone to the detection zone, and a denaturing reagent for nucleic acids present in the sample application zone.

39. Analytical element as claimed in claim 38, wherein the liquid transport zone includes an absorbent material that enables a chromatographic transport between the sample application zone and the detection zone.

40. Analytical element as claimed in claim 38, wherein the analytical element is designed as a test strip.

41. Analytical element as claimed in claim 38, wherein the detection zone contains a detection probe in an immobilized form that is complementary to the nucleic acids to be detected.

42. Analytical element as claimed in claim 38, wherein the denaturing reagent contains a base.

43. Analytical element as claimed in claim 38, wherein the denaturing reagent contains a base and a chaotropic substance.

44. Analytical element as claimed in claim 38, wherein the denaturing reagent contains a chaotropic substance.

45. Analytical element as claimed in claim 38, wherein denaturing reagent is impregnated in the sample application zone.

46. Analytical element as claimed in claim 38, further comprising a neutralizing reagent between the sample application zone and the detection zone.

* * * * *